US007494675B2

(12) United States Patent
Abbas et al.

(10) Patent No.: US 7,494,675 B2
(45) Date of Patent: Feb. 24, 2009

(54) PROCESS FOR THE PRODUCTION OF ANIMAL FEED AND ETHANOL AND NOVEL ANIMAL FEED

(75) Inventors: Charles Abbas, Champaign, IL (US);
Thomas P. Binder, Decatur, IL (US);
Kyle E. Beery, Decatur, IL (US);
Michael J. Cecava, Decatur, IL (US);
Perry H. Doane, Decatur, IL (US);
David P. Holzgraefe, Quincy, IL (US);
Leif P. Solheim, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 279 days.

(21) Appl. No.: 11/405,724

(22) Filed: Apr. 18, 2006

(65) Prior Publication Data
US 2006/0251764 A1    Nov. 9, 2006

Related U.S. Application Data

(60) Provisional application No. 60/672,779, filed on Apr. 19, 2005.

(51) Int. Cl.
*C12G 3/00* (2006.01)
*C12C 11/00* (2006.01)
*C12P 7/06* (2006.01)

(52) U.S. Cl. .............................. 426/12; 426/11; 426/16; 426/31; 426/53; 426/624; 424/750; 435/68.1; 435/72; 435/161

(58) Field of Classification Search ........................ None
See application file for complete search history.

(56) References Cited

U.S. PATENT DOCUMENTS

| 3,958,016 | A | * | 5/1976 | Galle et al. .................... 426/61 |
| 4,806,475 | A | | 2/1989 | Gould |
| 5,188,673 | A | | 2/1993 | Clausen et al. |
| 6,110,323 | A | | 8/2000 | Marsland |
| 6,428,828 | B1 | * | 8/2002 | Jackson et al. ................. 426/18 |
| 6,638,544 | B2 | * | 10/2003 | Vandana et al. ............. 424/757 |
| 6,962,722 | B2 | * | 11/2005 | Dawley et al. ................ 426/53 |
| 7,014,875 | B2 | * | 3/2006 | Rubio et al. ................... 426/52 |
| 2003/0232109 | A1 | | 12/2003 | Dawley et al. |
| 2004/0091983 | A1 | | 5/2004 | Veit et al. |
| 2004/0187863 | A1 | | 9/2004 | Langhauser |
| 2005/0118692 | A1 | * | 6/2005 | Kinley et al. ................ 435/161 |

OTHER PUBLICATIONS

Boissaid, A.L. et al., Steam Pretreatment of Douglas-Fir Wood Chips, Applied Biochemistry and Biotechnology, 84-86, p. 693-705, 2000.
Wu, M.M. et al., Optimization of Steam Explosion to Enhance Hemicellulose Recovery and Enzymatic Hydrolysis of Cellulose in Softwoods, Applied Biochemistry and Biotechnology, 77-79, p. 47-54, 1999.
Singh, V. et al., Recovery of Fiber in the Corn Dry-Grind Ethanol Process: A Feedstock for Valuable Coproducts, Cereal Chemistry, 76, p. 868-872, 1999.
Garrote, G. et al., Manufacture of Xylose-Based Fermentation Media from Corncobs by Posthydrolysis of Autohydrolysis Liquors, Applied Biotechnology, 95, p. 195-207, 2001.
Hespell, R.B. et al., Hydrolysis by Commercial Enzyme Mixtures of AFEX-Treated Corn Fiber and Isolated Xylans, Applied Biochemistry and Biotechnology, 62, p. 87-97, 1997.
Dale, B.E. et al., Hydrolysis of Lignocellulosics at Low Enzyme Levels: Applications of the AFEX Process, Bioresource Technology, 56, p. 111-116, 1996.
Enayati, N. et al., Enzymatic Saccharification of Soybean Hull-Based Materials, Biotechnology Process 11, p. 708-711, 1995.
Jung G. et al., Impact of Accessibility and Chemical Composition on Cell Wall Polysaccharide Degradability of Maize and Lucerne Stems, Journal of the Science of Food and Agriculture, 80, p. 419-427, 2000.
Ladisch, M.R. et al., Process Considerations in the Enzymatic Hydrolysis of Biomass, Enzyme and Microbial Technology 5, p. 82-102, 1983.
Males, J.R., Optimizing the Utilization of Cereal Crop Residues for Beef Cattle, Journal of Animal Science 65, p. 1124-1130, 1987.
Wanapat, J.M. et al., A Comparison of Alkali Treatment Methods to Improve the Nutritive Value of Straw. I. Digestibility and Metabolizability, Animal Feed Science and Technology 12, p. 295-309, 1985.
Alfani, F. et al., Comparison of SHF and SSF Processes for the Bioconverstion of Steam-Exploded Wheat Straw Journal of Industrial Microbiology & Biotechnology 25, p. 184-192, 2000.
Cameron, M.G. et al., Effects of Treating Oat Hulls with Alkaline Hydrogen Peroxide on Intake and Digestion by Mid-Lactation Dairy Cows, Journal of Dairy Science 74, p. 177-189, 1991.
Cameron M.G. et al., Effects of Feeding Alkaline Hydrogen Peroxide-Treated Wheat Straw-Based Diets on Digestion and Production by Dairy Cows, Journal of Dairy Science 73, p. 3544-3554, 1990.
Saha, B.C. et al., Enzymes in Lignocellulosic Biomass Conversion, in ACS Symposium Series 666, Fuels and Chemicals from Biomass, Saha, B.C. and Woodward, J eds., American Chemical Society, Washington, D.C. 1997.
Saha, B.C. et al., Enzymology of Xylan Degradation in ACS Symposium Series 723, Biopolymers, Imam, S.H.; Greene, R.V.; and Zaidi, B.R. eds., American Chemical Society, Washington, D.C. 1999.
Szakacs, G. et al., Solid-State Enzymes for Fiber Hydrolysis in ACS Symposium Series 769, Glycol Hydrolases for Biomass Conversion, Himmel, M.E.; Baker, J.O.; Saddler, J.N. eds., American Chemical Society, Washington, D.C. 2001.

* cited by examiner

*Primary Examiner*—Herbert J. Lilling
(74) *Attorney, Agent, or Firm*—Buchanan Ingersoll & Rooney PC; Craig G. Cochenour; Duane A. Stewart, III

(57) ABSTRACT

A method for the production of ethanol and a modified animal feed is provided. The method replaces the starch in known corn-based animal feed with biomass fiber treated to make it more digestible by animals. The process includes wherein the pericarp and germ are removed from the corn kernel and processed for by-products. The starch and protein are also removed and separated. The starch is then fermented and distilled to ethanol and stillage. The bioavailable modified animal feed comprises the pericarp and germ removed from corn kernels and optionally by-products of the pericarp and germ processing, and lignocellulosic materials. The modified animal feed may optionally include energy materials such as animal and vegetable fats, vegetable soapstocks, or glycerin, and combinations thereof.

14 Claims, 6 Drawing Sheets

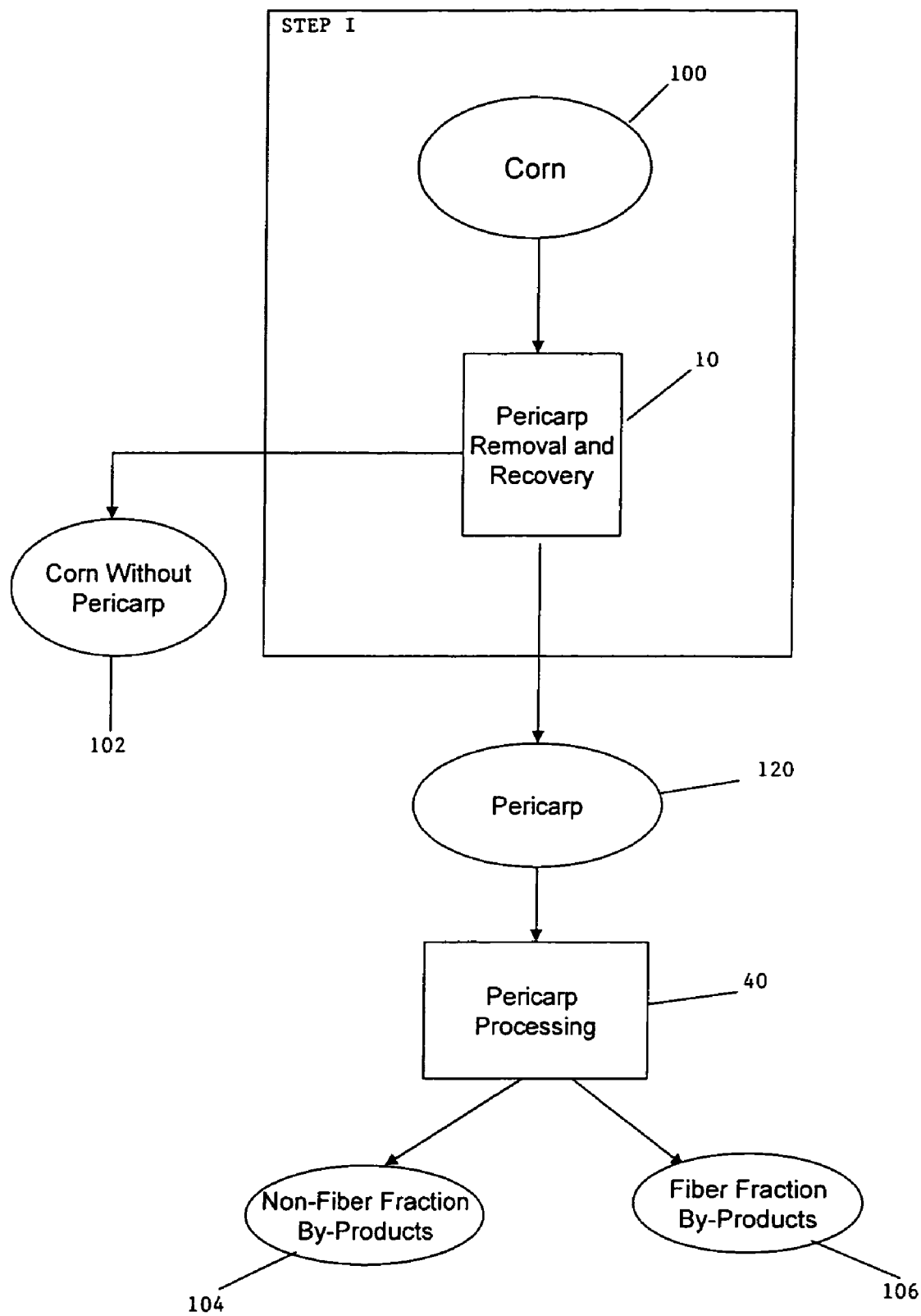
FIG. 1: Pericarp Removal

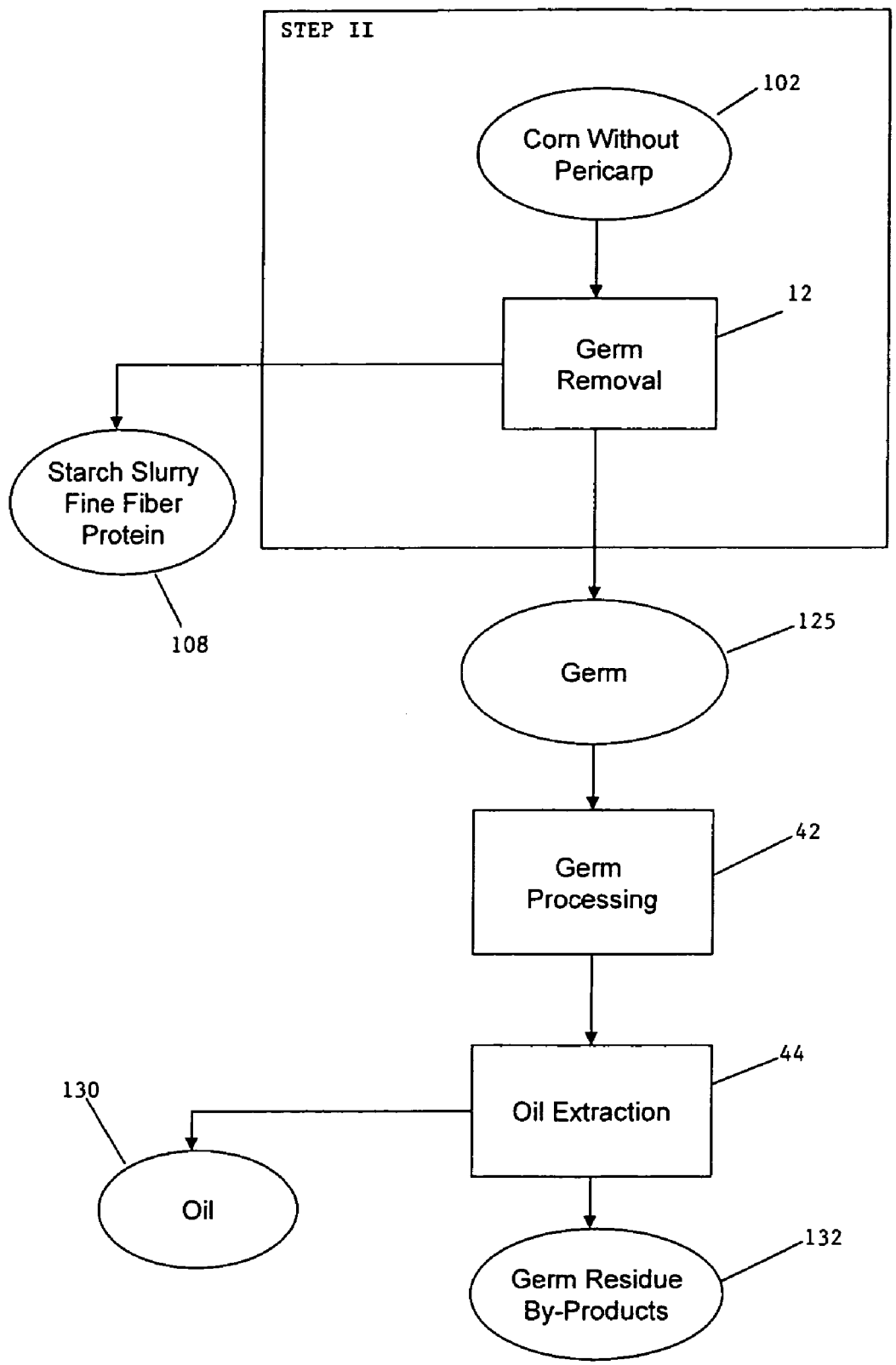
FIG. 2: Germ Removal

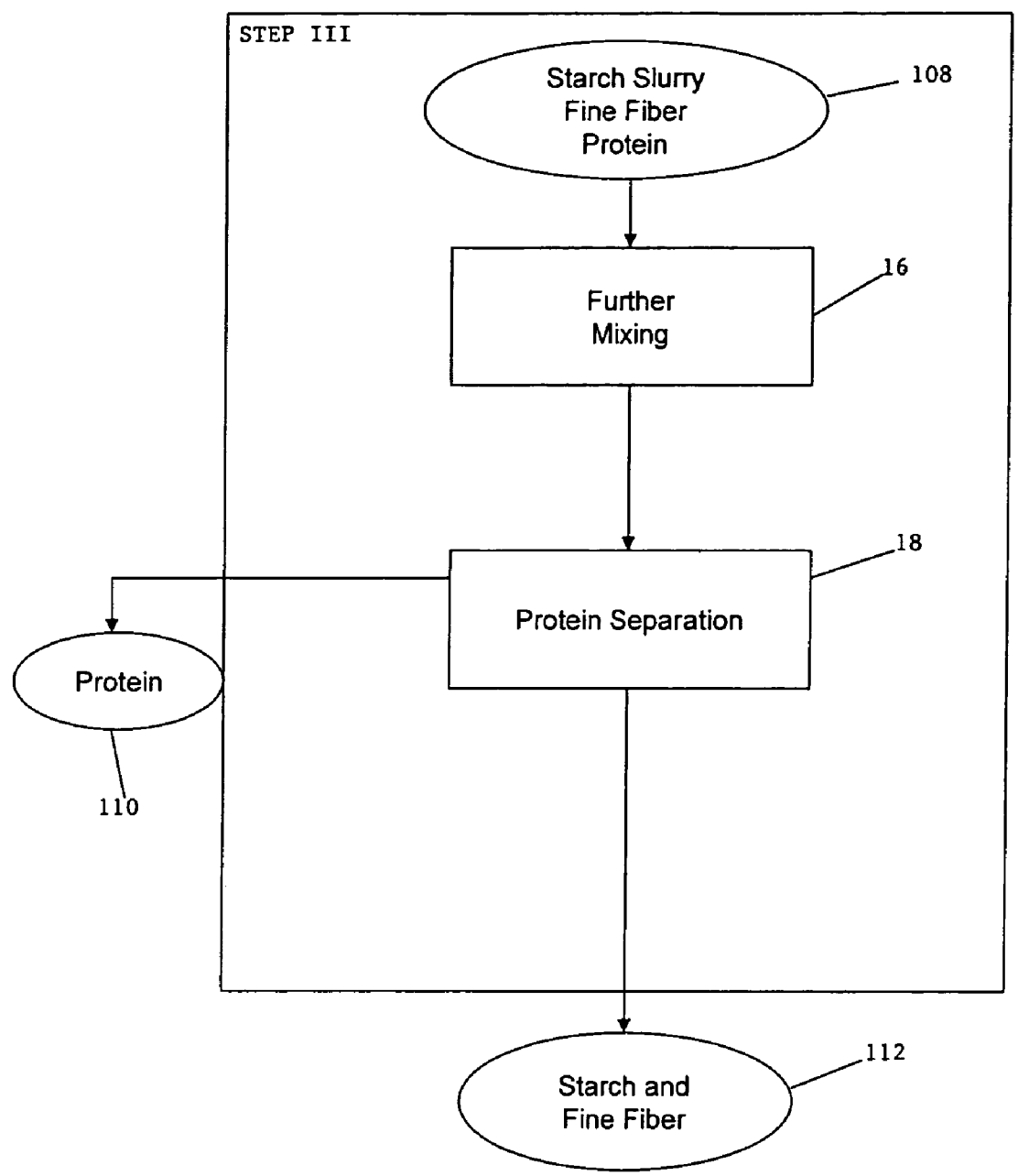
FIG. 3: Starch Processing and Separation

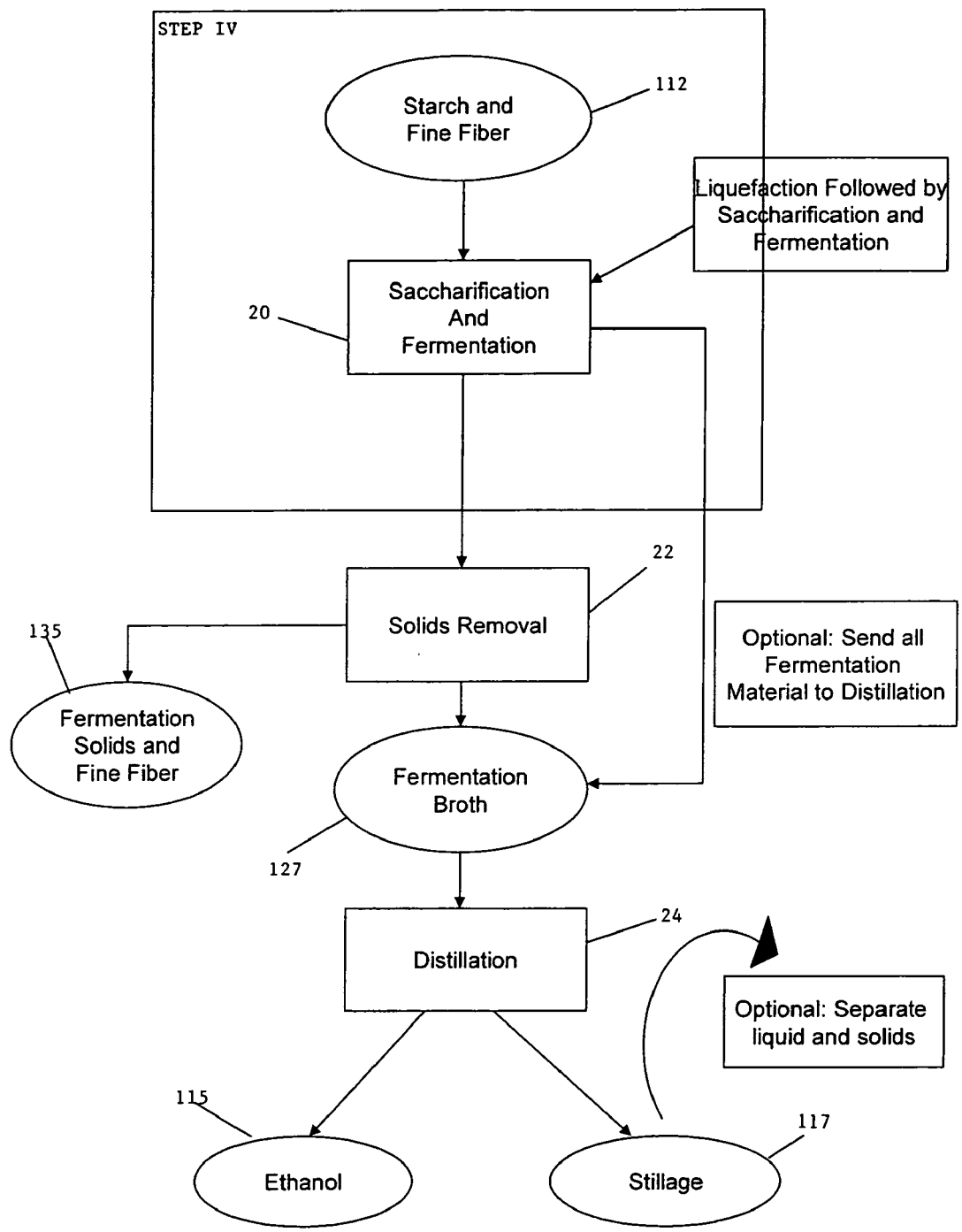
FIG. 4: Starch Hydrolysis and Fermentation and Production of DDG/DDGS

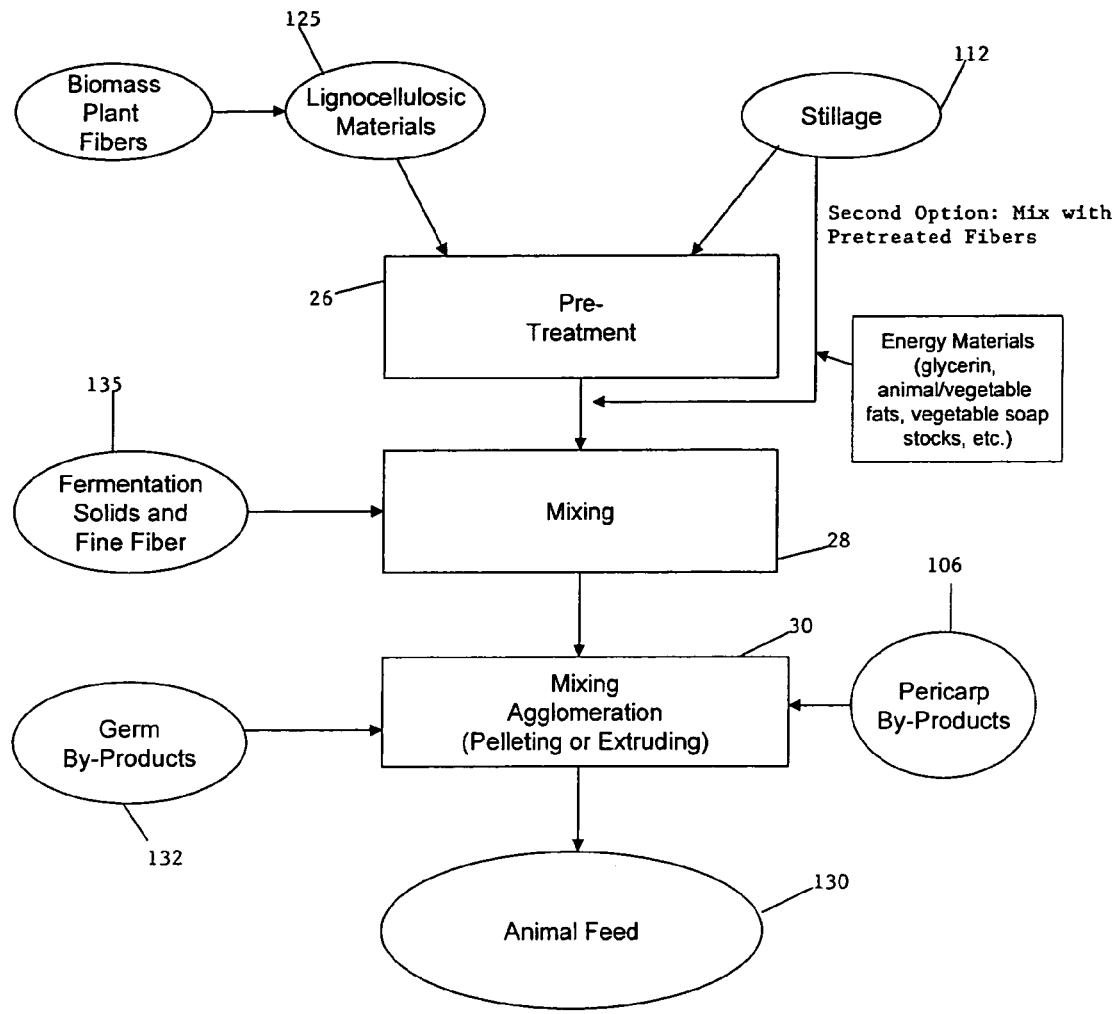
FIG. 5: Production of New Feed from Corn Dry Milling Plant Fibers

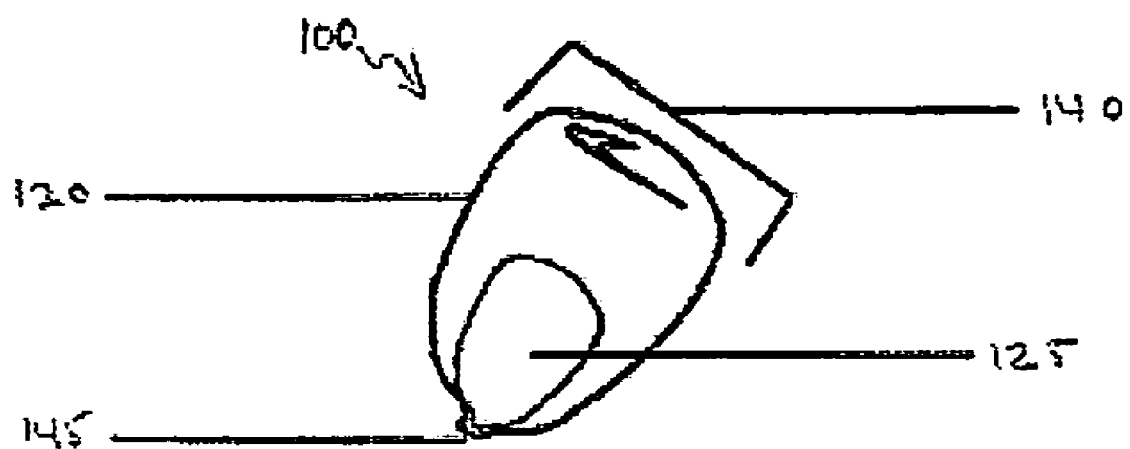
FIG. 6 : Corn Kernel

PROCESS FOR THE PRODUCTION OF ANIMAL FEED AND ETHANOL AND NOVEL ANIMAL FEED

CROSS-REFERENCE TO RELATED APPLICATION

This application is a nonprovisional of and claims the benefit of priority to U.S. Provisional Patent Application Ser. No. 60/672,779, filed on Apr. 19, 2005, entitled "Process For The Production Of Animal Feed And Ethanol And Novel Animal Feed", having the same named applicants as inventors, namely, Charles Abbas, Thomas P. Binder, Kyle E. Beery, Michael J. Cecava, Perry H. Doane, David P. Holzgraefe, and Leif P. Solheim. The entire contents of U.S. Provisional Patent Application Ser. No. 60/672,779 are incorporated by reference into this nonprovisional utility patent application.

STATEMENT OF FEDERALLY SPONSORED RESEARCH

The U.S. Government has a paid-up license in this invention and the right in limited circumstances to require the patent owner to license others on reasonable terms as provided for by the terms of Award Number NRCS 68-3A75-3-140 awarded by U.S.D.A.

BACKGROUND OF THE INVENTION

1. Field of the Invention

This invention relates to methods of producing a novel bioavailable modified animal feed and expanding ethanol production, and a novel bioavailable modified animal, preferably cattle, feed.

2. Description of the Background Art

Within the new Energy Bill is a Renewable Fuels Standard requiring renewable fuel production of 7.5 billion gallons by 2012. This increase from the current level of 3.8 billion gallons of ethanol will almost certainly take place by increasing the amount of ethanol produced from corn, specifically from dry-milling of corn. Dry milling of corn is the most cost effective way to increase the production of ethanol, and produces the fewest and lowest volume of by-products.

Over 11 billion bushels of corn were harvested in 2005; however, only approximately 2.6 billion bushels were processed by wet or dry milling, with only approximately 1.4 billion bushels processed for ethanol production. The remaining 8.4 billion bushels of corn are utilized mainly as animal feed, with over 2 billion bushels as cattle or dairy feed. Corn is fed to provide an inexpensive energy and protein source to feeder and dairy cattle; however, the starch in corn is readily metabolized by the rumen microorganisms. These organisms ferment the starch to organic acids, which at high concentrations can lead to acidosis in the cattle. Based on research completed by ADM Alliance Nutrition, approximately 550 million bushels could be diverted from use as cattle or dairy feed to ethanol, if a >60% digestible corn replacement could be produced. If the 550 million bushels of corn were to be diverted to produce ethanol by dry milling, an additional 1.5 billion gallons of ethanol could be produced. Based on a current production of 3.8 billion gallons of ethanol in 2006, this would increase the total ethanol production by 40% without increasing corn acreage planted.

The present invention provides for several cost effective ways that facilitate the expansion of ethanol dry mill corn refineries while maintaining adequate cattle feed supplies to the market. This invention also outlines new approaches to processing corn in dry mills. Part of the plan to maintain cattle feed supplies includes treating various biomass fiber sources to increase the digestibility for cattle, to provide a corn replacement pellet.

By diverting this corn from cattle feed to ethanol production, two issues will arise. The first issue is the loss of energy from starch for cattle feed, and the second is the additional production of corn dry milling byproducts, which will greatly over-saturate the animal feed market. Both of these issues can be addressed by upgrading the dry milling by-products to an enhanced cattle feed to replace the energy from starch.

To replace the estimated 550 million bushels of corn which could be diverted annually from dairy and beef cattle feed, an equivalent amount of bio-available feed would need to be substituted for the corn. The 550 million bushels of corn are equivalent to 26.4 billion pounds total, comprising approximately 19.6 billion pounds of starch, and 3.09 billion pounds of lignocellulosics. By the current dry milling process, 550 million bushels of corn would yield 9.2 billion pounds of distillers dried grains (DDG) and distillers dried grains with solubles (DDGS), which are the major by-products of the dry-milling process. Therefore, an additional 17.2 billion pounds of similarly bio-available feed would need to be made up by currently available lignocellulosics, such as soybeans hulls, corn stover, or wheat straw. The energy content of the feedstocks would also need to be determined to ensure an equivalent amount of feed energy value for the new bio-available cattle feed.

Cattle are able to utilize the protein from DDG and DDGS in their diet. The cellulose and hemicellulose are broken down enzymatically in the rumen of the animal as a source of mono- and di-saccharides. The DDGS also contain vitamins and minerals that are beneficial to animals such as cattle.

It is therefore an object of this invention to enable the expansion of ethanol production by corn dry-milling while ensuring adequate feed supply to the cattle market by supplementing the DDG and DDGS produced as a by-product of the dry-milling process with other agricultural processing by-products and pretreated agricultural residues.

The known in the art current method of corn dry-milling is composed of an initial cleaning step by screening (sieving) to remove small broken kernels and impurities and aspiration to remove light impurities for the corn followed by a grinding step utilizing a hammermill or a roller mill. The ground corn is generally heated to 125-150° C. for 10 seconds through a jet cooker at a pressure of about 5.1 bar and then held at 95° C. at ambient pressure for 10 minutes, with 2 times the mass of water added to the ground corn prior to jet cooking, and a high-temperature (from about 80° C. to about 99° C.) α-amylase enzyme (0.01% wt/wt addition) to liquefy the starch to oligosaccharides. The liquefied starch is then cooled to 30° C. and saccharified to glucose by utilizing a glucoamylase (0.01% wt/wt addition) enzyme while simultaneously fermented in a fermentation vessel with *Saccharomyces cerevisiae* to ethanol at ambient pressure and pH 4-5 for 48 hours. The insoluble pericarp, protein, tip cap, and germ are not separated during the processing and fermentation of the starch. The glucose is fermented primarily by yeast to ethanol with carbon dioxide as a co-product. The theoretical production is 0.51 wt % ethanol and 0.49 wt % carbon dioxide. The glucose concentration is between 200-350 grams per liter in the fermentation broth, which, when fermented, gives a final ethanol concentration of 13-23% on a volume ethanol/volume of fermentation broth basis. The ethanol is distilled at temperatures between 80 and 100° C. and 1.1 bar from the fermentation broth to a final ethanol concentration of 95% and then further dehydrated to 100% by passing the ethanol/water vapors through an adsorption system at 82° C. and at 1.1 bar. The water and solids in the fermentation broth is called stillage and leaves the bottom of the distillation column at ambient pressure and 80° C. The solids remaining in the fermentation broth (pericarp, protein, germ, and tip cap) are separated from the liquid utilizing a centrifuge and optionally dried through a gas-fired rotary drum dryer and agglomerated through a pellet mill or extruder to create distiller's dried grains, which are sold primarily as an animal feed.

SUMMARY OF THE INVENTION

The object of the invention will be accomplished by greater utilization of pretreated lignocellulosics, which are derived from current crops and existing agricultural processing operations, as animal feed. This invention creates a bio-available cattle feed by mixing pretreated agricultural processing by-products and pretreated agricultural residues.

Upgrading the DDG and DDGS can be achieved by mixing these by-products of the dry-milling process with thermochemically, chemically enzymatically and/or physically pre-treated corn stover, wheat straw, corn meal germ, soybean hulls, rice straw, oat hulls, solid edible bean byproducts, cottonseed hulls, barley hulls, other forage crop fibers, or other cellulosic biomass.

The composition of DDG and DDGS and other agricultural processing by-products and pretreated agricultural residues are found in Table 1 below.

TABLE 1

Approximate Feedstock Compositions

| Feedstock | Cellulose | Hemicellulose | Starch | Fat | Ash | Protein | Lignin | Pectin and Gums |
|---|---|---|---|---|---|---|---|---|
| Corn | 2.0% | 7.6% | 76.0% | 5.7% | 1.6% | 11.4% | 1.0% | |
| Corn Fiber Hulls | 16.0% | 40.0% | 18.0% | 3.0% | 3.0% | 11.0% | 4.0% | |
| DDG/DDGS | 22-26% | 24-28% | | 8-12% | 2.50% | 26-29% | 4.0% | |
| Corn Gluten Feed | | 25.1% | 23.0% | 3.3% | 8.2% | 23.9% | | |
| Corn Germ Meal | 12% | 25% | 12% | 3% | 3% | 22% | 2% | |
| Corn Stover | 38.0% | 25.0% | | 3.3% | 6.1% | 4.0% | 17.5% | |
| Soybean | 2.0% | 5.0% | | 18.8% | 5.5% | 42.8% | | 7-15% |
| Soybean Hulls | 46.0% | 18.0% | | 2.5% | 5.0% | 12.0% | 2.0% | |
| Wheat | 8.0% | 4.0% | 70.0% | 2.2% | 1.6% | 12.3% | 2.0% | |
| Wheat Straw | 35.0% | 24.0% | | | 6.0% | 4.0% | 25.0% | |
| Switchgrass | 33.5% | 26.5% | | | 6.4% | 5.3% | 18.1% | |
| Brown rice | 1.0% | 2.0% | 74.4% | 2.6% | 1.6% | 8.5% | | |
| Rice Hulls | 30.0% | 20.0% | | 0.8% | 16.3% | 3.2% | 21.4% | |
| Oat | 11.0% | 15.0% | 68.2% | 5.4% | 3.4% | 13.3% | 2.7% | |
| Oat Hulls | 30.0% | 34.0% | | 1.6% | 6.1% | 3.6% | 13.2% | |
| Cocoa Shells | 13.7% | 7.1% | | 8.3% | 15.3% | | 3.4% | 8.0% |
| Cottonseed Hulls | 59.0% | | | 1.7% | 2.8% | | 24.0% | |
| Barley | 5.0% | 13% | 78.8% | 3.9% | 2.2% | 12.8% | 2.0% | |

A pretreatment process is used to enhance the digestibility of the cellulosic materials by the cattle. A thermochemical treatment will partially hydrolyze the hemicellulose and cellulose portions of the stover/straw/hulls/biomass fibers. The partial hydrolysis of the cellulosic portion will cause the cellulose to become more susceptible to degradation by the bacterial cellulases in ruminants. Thermochemical pretreatment will decrease the crystallinity of the cellulose and render it more bio-available, and will also degrade the hemicellulose portions to oligosaccharide fractions. Chemical treatments utilizing acids, bases, or organosolvents can also improve carbohydrate digestibility through the hydrolysis of backbone sugar O-glycosidic linkages, release of side chain substituents, separation of hemicellulose from lignin, or solubilization of hemicellulose and lignin. Enzymatic treatments utilizing cellulosic degrading enzymes including but not limited to cellulase and hemicellulase will decrease polymer crystallinity thus improve bio-availability. The removal of substituents or hydrolysis of the polysaccharide backbone chain improves enzymic breakdown of the biomass fiber by providing increased access to the polymer backbone. Physical pretreatment will decrease the particle size to increase surface area for more efficient ruminant digestion. The pretreatment process may also increase the hydration capacity (liquid-holding ability) of the lignocellulosic materials. If this is the case, then energy-containing materials, preferably in liquid form, such as for example but not limited to animal fats, vegetable soapstocks, and/or glycerin, and combinations thereof, may be added to the pretreated lignocellulosic materials of the present invention.

In this manner, the cellulose may replace the starch that is diverted towards increased fuel ethanol production. Combining this bio-available cellulose with the DDG/DDGS would provide a sufficient feed for cattle. As is the case with current cattle feed, the new cattle feed would need to be milled and pelletized to provide a high-energy, high-density animal feed.

The corn diverted from cattle feed would be processed to ethanol by dry milling, thereby producing the DDG and DDGS as by-products. Dry milling is currently the most cost-effective way to expand the production of ethanol.

This invention also discloses methods to improve the dry milling process. As compared to wet milling, dry milling uses less water, generates fewer co-products, and is not as capital intensive. To enhance the economics of dry milling, new cost-effective ways of processing the corn prior to fermentation are desirable. The methods of this invention include removing the pericarp and separating the germ prior to grinding and wetting the remaining corn, thus maximizing the amount of co-products. This invention lowers the viscosity of the fermentation mash and allows for easier conversion of the starch to dextrose by reducing the dry solids. Also, this invention saves energy since the pericarp and germ do not need to be dried. In a further embodiment of this invention, the process includes wherein the separated germ and pericarp are further processed for oil and other valuable components prior to incorporation into the DDG/DDGS animal feed.

This invention overcomes three of the hurdles currently faced by efforts to convert lignocellulosics such as stover/straw/hulls/other biomass fibers to ethanol. Those hurdles are: first, the recalcitrance of cellulose to enzymatic degradation due to the lignin seal; second, the high amount of energy required to pretreat fibers to enhance their digestibility; and third, the economic problems associated with the transport of low energy density biomass.

The first and second problems are addressed by the bacterial consortium present in the cattle rumen, which produce efficient cellulase complexes and other fibrolytic enzymes for degrading these streams without extraneous fermentations. With a minimum pretreatment, and thus a minimum energy input, the digestibility is greatly increased by the combination of the pretreatment and bacterial rumen enzymes. The third problem is addressed by locating processing plants that will convert the DDG/DDGS and straw/stover/hulls/other biomass fibers to an acceptable animal feed in areas where the straw/stover/hulls, cattle, and feed mills are presently available or located, thus minimizing expenses associated with transporting feedstocks with a low energy density. The soy hulls may be a feedstock utilized because they are derived from soybean processing at soybean crushing facilities and corn germ meal derived from corn wet-milling facilities, therefore are readily available.

This invention provides an improved feed with a variable composition, wherein the exact composition is dependent on which crops are grown nearby. This will depend on the location of the corn dry-mill, the soybean processing plant, and the plant fiber biomass pretreatment facility. Similarly, corn germ meal from the corn wet-milling process may also be utilized. This process will create new byproduct streams from the modified dry-mill, and will combine those materials with pretreated plant fibers that contain significant quantities of carbohydrates. This new feed material will contain a reduced amount of starch, and will therefore not be as conducive to rumen acidosis thereby allowing the animal to utilize more of the feed. With an increased hydration capacity of the plant fibers, energy ingredients, preferably in a liquid form, such as animal fats, vegetable soapstocks and/or glycerin, and combinations thereof, may be added to the referenced mixing steps in FIG. 5 to develop novel feeds with applications for monogastrics, as well. Also, this invention creates a new dry-milling scheme with novel by-products.

BRIEF DESCRIPTION OF THE DRAWINGS

FIG. 1 shows Step I of the integrated process in which the pericarp is removed from the corn kernel and optionally processed to remove by-products.

FIG. 2 shows Step II of the integrated process in which the germ is removed from the corn kernel and optionally processed to remove by-products.

FIG. 3 shows step III of the process in which the protein is removed and further milling occurs.

FIG. 4 shows Step IV of the process in which the starch of the corn kernel is saccharified and fermented, and optionally, wherein the fermented beer is distilled to produce ethanol.

FIG. 5 shows Step V of the process in which pretreated lignocellulosic material is mixed with by-products of previous steps of the process to produce an improved cattle feed.

FIG. 6 shows a schematic representation of a corn kernel showing the constituent parts thereof.

DETAILED DESCRIPTION OF THE INVENTION

The present invention is a method for processing corn kernels comprising the steps of removing the pericarp from the corn kernels, removing the germ from the corn kernels resulting in a starch and a protein, separating the starch and the protein from each other, and saccharifying and fermenting the starch to produce a fermented starch broth. Preferably, the method of this invention comprises liquefying the separated starch before the saccharification and fermentation of the starch. A flow chart of the improved processes of this invention is found in FIGS. 1-5. The method of the present invention for processing corn kernels is preferably divided into five general steps: pericarp removal from the corn kernel; germ removal from the corn kernel resulting in a starch and a protein fraction; separation of the starch and protein; fermentation of the starch to ethanol; and pericarp processing and biomass fiber pretreatment. The corn is first processed to remove the pericarp (and likely the tip cap) from the remaining starch, protein, and germ by a tempering step followed by milling and separation. The tempering step can include a chemical tempering by utilizing lactic acid at ambient temperatures and pressures, 3% wt/wt gaseous or liquid ammonia addition at ambient temperatures and pressures, or 10% water addition at ambient temperatures and pressures. The milling step could include processing with a Fitz Comminutor Mill with a ¼ inch screen, a Ferrell-Ross Flaking mill with a gap setting of 1.1 or a Ferrell-Ross flaking mill with a gap setting of 3. After the milling step, the milled mixture could be aspirated with a 1-inch differential on a Kice aspirator to separate the starch granules fraction and the pericarp fraction from the heavier endosperm and germ fraction. Alternatively, the milled fraction could be sieved over a combination of 10 and 40 mesh screens to separate the larger pericarp fraction (larger than 10 mesh) from the endosperm and germ fraction (larger than 40 mesh, smaller than 10 mesh) and from the starch granules fraction (smaller than 40 mesh). Further milling and separation steps can lead to further purified corn fractions.

The pericarp is processed to obtain chemicals, food fiber, feed fiber, nutraceutical and possibly pretreated to enhance the digestibility by heating the pericarp to about 150° C. with 1% sulfuric acid for about 30 minutes to yield an oligosaccharide containing mixture, extracting the pericarp in a counter-current extractor with ethanol at about 70° C. or alkaline ethanol at about 70° C. to yield a corn fiber oil or a ferulic acid fraction, or hydrolyzing the corn fiber with cellulase, hemicellulase, amylases, and protease enzymes to obtain a fermentable sugar mixture. A combination of the previous treatments could also be utilized, such as heating the pericarp to about 150° C. with 1% sulfuric acid for about 30 minutes followed by adjusting the pH of the mixture to a pH of about pH 5 and adding enzymes as described herein to obtain a sugar mixture.

Next, the germ is separated from the starch and protein, and separately processed to remove oil and sterols. This can occur by processing the corn endosperm and germ fraction as separated above by further milling through a Ferrell-Ross cracking mill with a gap setting of 3 to reduce the endosperm size and then sieve the resulting mixture over a 40 mesh screen to separate the starch fraction (smaller than 40 mesh) from the germ fraction (larger than 40 mesh). The remaining starch and protein can be separated and the starch can be extracted to remove the oil and sterols and then fermented. Optionally, the starch and protein may both be sent to the ethanol fermentation. The starch and protein fraction can be liquefied by jet cooking from about 120 to about 150° C. with 0.01% α-amylase at a pressure of about 5.1 bar for about 10 seconds with 2 times added weight of water followed by holding the enzyme-starch-corn protein mixture at about 95° C. for about 10 minutes. The protein-liquefied starch stream can then be nanofiltered through a filter with a 1000 molecular weight cutoff to separate the protein from the liquefied starch. The starch can be fermented by adding 0.01% glucoamylase and inoculating with *Saccharomyces cerevisiae* to the liquefied starch fraction at about 30° C. and about a pH of pH 5 for about 48 hours. The ethanol fermentation broth can be processed to remove the solids by centrifugation and then distilled at temperatures between about 80 and 100° C. to remove the ethanol or it can optionally be distilled first and then centrifuged. The germ fraction can be processed by extraction of the germ with a 7:1 hexane to germ ratio in a counter-current Crown extractor at ambient pressure for about 1 hour at about 60° C. The germ and hexane are separated over a moving screen, and the germ can be dried in a desolventizer at about 150° C. at ambient pressure for about 30 minutes to release any remaining hexane. The recovered hexane can be condensed and reused. The oil-containing hexane can be processed by methods known in the art to separate, purify and refine the oil fraction. Finally, the processed germ, pericarp, and other solids are mixed and then blended with, for example but not limited to, thermochemically pretreated biomass fibers, such as for example but not limited to, soybean hulls, corn stover, wheat straw, and the like, or other lignocellulosic materials or crop fibers, before or after thermochemical treatment to produce a bioavailable modified feed. The thermochemical treatment of the biomass fibers may be hydrolyzed at about 150° C. for about 30 minutes at a pressure of about 5.1 bar at about a 30% solids content in a reactor rotating at 1 RPM. Optionally, the pericarp may be processed to obtain chemicals and then pretreated to enhance digestibility for feed, nutraceutical, and food applications. If the pericarp is thermochemically hydrolyzed at about 150° C. for about 30 minutes at a pressure of about 5.1 bar at about 30% solids in a reactor rotating at 1 RPM, an oligosaccharide containing mixture can be separated by processing with a Vincent screw-type press. This oligosaccharide containing mixture can be heated in an agitated reactor (100 RPM) at about 121 °C. with 1% added sulfuric acid for about 30 minutes at a pressure of about 2.1 bar to produce a monosaccharide containing liquid with glucose, xylose, arabinose, galactose, and mannose. This sugar mixture can be fermented to ethanol or other products. If the pericarp is extracted with ethanol at ambient pressure at about 70° C. for about 1 hour, the ethanol extract will contain phytosterols, free fatty acids, and triglycerides.

Referring to FIG. 1 in which Step I of the process is shown, in box 10, pericarp 120 is removed from, for example but not limited to, corn kernels 100. One possible method of separating pericarp 120 is by alkali debranning, such as for example, by adding a 1% sodium hydroxide solution in a 7:1 alkali solution to corn kernels mixture at ambient pressure and about 60° C. for about 10 minutes. Alternately, a 3% aqueous ammonia solution can be added at about 60° C. for about 10 minutes at ambient pressure with agitation at a 7:1 ratio of ammonia solution to corn kernels. This method, for example but not limited to, may be accomplished with a hot caustic soda solution or aqueous ammonia solution, which would hydrolyze the chemical bonds between pericarp 120 and endosperm 140 (see FIG. 6—corn kernel example components) so that mechanical equipment as detailed herein can separate the components. Acid debranning with mineral or organic acids is able to penetrate into kernel 100 and break the bonds between pericarp 120 and endosperm 140. This could be accomplished with 1% sulfuric, acetic, or lactic acid in a 7:1 ratio of acid solution to corn kernels at about 60° C. for about 10 minutes at ambient pressure. Finally, another example of the method of the this invention includes first conditioning of kernel 100 with steam or hot (having a temperature of from about 50° C. to about 99° C.) water (tempering) at about a 10% wt mixture of water to corn kernels at about 60° C. for about 1 hour, followed by milling as detailed herein to abrade pericarp 120 from the remainder of corn kernel 100. All of the previous methods need to be followed by a physical separation step, which will use a mill, as detailed herein. The mills that may be used, such as for example but not limited to, include a disc mill, a cracking roll mill, a flaking mill, a Fitz comminutor mill, or a Boston shear pump. The milling step may be followed by an additional separation step, which may utilize a vacuum suction separator, a cyclone, a hydroclone, a sieve with 10 and 40 mesh sizes, or an aspirator. The corn kernel fractions without the pericarp 120 are the result of Step I of the process of this invention.

The separated fractions of the corn will be processed for further by-products. The removed pericarp 120 can be solvent extracted to remove by-products 104, such as phytosterols, if they are present, and/or treated with aqueous acid or base or with a acidic or basic solvent, all of which solvents are known in the art, at about 70° C. for about 1 hour at ambient pressure in a Crown counter-current extractor for the extraction of the hemicellulose, either oligosaccharides or the intact hemicellulose, other lignins, and other lignin precursors, or to release ferulic acid or coumaric acid from the hemicellulose chains. These components could be separated by ion exchange chromatography from the remaining liquid, or other lignin precursors. This can be done by treating the pericarp with alkali, ethanolic alkali, acid or ethanolic acid, depending on the component of interest. By-products 106 comprised mainly of fiber, are used later in the integrated process as a component of the final cattle feed product.

Referring now to FIG. 2 showing Step II of the process, following removal of pericarp 120, germ 125 will be removed from endosperm 140 in box 12, as detailed above. For example but not limited to, a method that may be used to separate the components is lactic acid steeping, which allows for the hydrolysis of chemical bonds between endosperm 140 and germ 125 (FIG. 6). This could be accomplished by adding a 1% lactic acid solution at a 2:1 ratio of solution to germ and endosperm mixture at about 70° C. for about 1 hour. Enzyme hydrolysis for the separation of endosperm 140 and germ 125 can also be used wherein 0.01 wt % high temperature (80° C. to 99° C.) α-amylase is added to about a 30% dry solids germ-endosperm mixture, and the mixture heated from about 120 to about −150° C. for about 10 seconds to liquefy the starch. The germ fraction could then be removed by passing the solution through a screen to separated out the germ pieces. Again, the methods described may need to be followed by a physical separation step using a mill or sieve. The mills that may be used include, for example but not limited to, a disc mill, a cracking roll mill, a flaking mill, and a Boston shear pump. The milling may also be followed by a separation step utilizing a vacuum suction separator, a cyclone, a hydroclone, or an aspirator. The removal of germ 125 leaves a starch slurry, fine fiber and protein with optionally an aleurone layer. The output of Step II of the process is a starch slurry, fine fiber and protein, and optionally an aleurone layer 108.

Germ 125 can be processed, in box 42 could be further processed for extraction of oil and other nutraceuticals 130, by practices know in the art, such as by hexane, heptane, ethanol, other organic solvents, sub-critical water extractions, supercritical $CO_2$, etc. Generally, the germ is extracted as detailed above at about 60° C. with a 7:1 ratio of hexane to germ in a Crown counter-current extractor for about 1 hour at ambient pressure. The processed germ results in oil 130 containing triglycerides and tocopherols and germ by-product 132, comprised primarily of fiber, which may also be used later in the integrated process as a component of the improved cattle feed.

In FIG. 3, showing Step III of the process, protein 110 will be separated from the starch slurry, fine fiber and protein mixture 108. In box 16 further milling may be required to reduce starch 112 to starch granules, and in box 18, protein 110 is extracted, leaving starch 112 and fine fiber. Starch 112 and protein 110 can be separated by clamshell and centrifuge processing if they are in a slurry, or by solubilization of starch 112 by enzyme saccharification or jet cooking as detailed above. Another method of separating the protein and starch is the solubilization of the starch by enzyme saccharification, starch 112 will be hydrolyzed to oligosaccharides or, in the case of jet cooking, starch 112 will be gelatinized and solubilized. Starch 112 and protein 110 can also be separated by membrane filtration. This step results in starch 112 and fine fiber FIG. 4 shows Step IV of the process. In box 20, the starch portion of starch and fine fiber 112 will be saccharified and fermented as set forth herein. Optionally, in box 22, the solids, comprising the fiber components and fermentation solids 135, are separated, and, in box 24, the fermentation broth 137 is distilled to ethanol 115, wherein the distilled ethanol has a proof ranging from about 180 to about 190 proof, or from about 90% to about 95%. Alternatively, in box 20, the fermentation broth containing the liquids and solids can be distilled first, as in box 24, and then the stillage 117, containing the fermentation solids and fine fiber, 135, can be separated from the ethanol and then further separated from the remaining liquid. This step may be accomplished using advanced fermentation techniques to improve the yield and efficiency of the fermentation. Stillage 117 is a by-product of the distillation process. This can be evaporated to form a concentrate, which is added to the fermentation solids and fine fiber. This mixture may be dried to produce a modified Distillers Dried Grains (DDG) or Distillers Dried Grains with Solubles (DDGS) for animal feed.

In Step V of the process of the present invention, shown in FIG. 5, biomass fibers obtained from plants, such as various lignocellulosic materials, such as corn stover, wheat straw and soybean hulls 125 form the basis of the improved modified animal feed of the invention. In a preferred embodiment of the invention, these biomass fiber materials can be pretreated, in box 26, by aqueous acid, base, or mechanical methods, to increase the digestibility of those materials. The biomass fiber materials can be treated by adding 5 wt % calcium hydroxide to the biomass fiber samples and then heating at about 150° C., at a pressure of about 5.1 bars for about 30 minutes with direct steam injection in a rotating reactor, rotating at 1 RPM. Alternately, the biomass fiber materials can be treated by adding 3 wt % ammonia to the biomass fiber sample and treated as above. Alternatively, the biomass fiber samples can be treated with 1% sulfuric acid and treated as above. Alternatively, the biomass fiber materials can be processed through a mechanical macerator or extruder to reduce the particle size. Alternatively, the biomass fiber materials can be process through a mechanical macerator or extruder with any of the above chemicals added. Preferably, the pretreatment can be accomplished by mixing the biomass fibers with stillage at about 80° C. 117 from the distillation of the fermentation broth from box 24 in Step IV, and heating the mixture further to about 150° C. with the optional addition of other chemicals, such as enzymes, known by those skilled in the art to further enhance digestibility of the material for cattle as set forth herein. The mixture can be heated for about 30 minutes at a pressure of about 5.1 bar in a rotating reactor, rotating at 1 RPM. Other physical and thermochemical methods, know by those skilled in the art, may be employed to increase the digestibility of the lignocellulosic materials or the materials remaining after the corn milling process of this invention. The hydration capacity (liquid holding capability) of the biomass fibers, such as the lignocellulosic materials (hulls/straw/stover/other biomass fibers) may also be increased by this process, so energy-containing materials, preferably in a liquid form, such as animals fats, vegetable soapstocks, and/or glycerin, and combinations thereof, may be added to increase the caloric content of the modified animal feed of the present invention.

In box 28 the pretreated lignocellulosic materials 125, previously mixed with the stillage 112, are mixed with energy containing materials, preferably in a liquid form (for example, animal/vegetable fats, glycerin, and soapstocks, etc.), fermentation solids and fine fiber 135 (DDG/DDGS) and then agglomerated (pelleted or extruded) to form the basic animal, such as for example cattle, feed product of this invention. Germ by-products 132 and pericarp by-products 106 may optionally be mixed in, at box 30, to make up another embodiment of the bioavailable modified animal feed 130 of the present invention.

In another embodiment of this invention, the by-products from Steps I and II, the processed pericarp 120 and germ 125 respectively, and any other solids from the corn milling process can also be optionally pretreated as described herein (this step not shown in figures).

Those persons skilled in the art shall appreciate that various methods may be used to pretreat the biomass fibers, including alkaline treatments, acid treatments, heat treatments, mechanical treatments, and enzyme treatments on many different types of lignocellulosic materials, including soybean hulls, soybean straw, wheat straw, wheat hulls, wheat midds, wheat C starch, corn fiber hulls, corn gluten feed, corn stover, corn cobs, corn germ meal, barley mill waste, oat hulls, oat straw, cottonseed, cotton gin waste, rice hulls, rice straw, sugar cane bagasse, sugar beet pulp, orchard grass, fescue, switchgrass, alfalfa, other forage crop fibers, etc. as set forth herein. The alkaline treatments may include, but are not limited to, treating the lignocellulosic materials with liquid caustic or liquid caustic and peroxide to help degrade the fibrous plant biomass, or with gaseous ammonia. The acid treatments include dilute acid addition to the biomass and optional heating to reduce the crystallinity of the cellulose and to break down the polysaccharides to oligosaccharides. The physical/mechanical treatment can optionally use steam explosion and/or mechanical size reduction to increase the surface area for attack by rumen microbial flora enzymes, and also to reduce the crystallinity of the cellulose, which will increase the digestibility of the cellulose. Finally, the enzyme treatment will be used to degrade the biomass to oligosaccharides. Those persons skilled in the art shall appreciate that these treatments can be used in various combinations.

Corn kernels 100 may also be optionally pretreated by treatment with various chemicals, alkalis, acids and enzymes, after which the corn will be milled to first remove pericarp 120 and then to remove germ 125. The equipment used for milling and separating includes for example but not limited to cracking roll mill, flaking mill, aspirator, conditioner, and a Boston shear pump. After pericarp 120 and germ 125 have been separated, the remaining starch/protein mixture can be processed to separate the starch from the protein, or could be heat treated with steam and enzymes to convert the starch to oligosaccharides. After the fermentation of the glucose to ethanol, the solids, mainly yeast, in the fermentation media will be separated by using a solid bowl centrifuge. The yeast can be recycled to the fermentor vessel or used in other applications to produce food or feed flavors. The yeast or portions of the processed yeast may also be mixed into the animal feed product, 130. The ethanol-containing fermentation broth will then be distilled, and the remaining stillage at about 80° C. will preferably be used as a water source for the thermochemical hydrolysis of the biomass fibers. The biomass fibers will then be mixed with the solids from the dry-milling process to create an enhanced animal feed.

To market the bioavailable modified animal feed of the present invention comprising the pericarp removed from corn kernels, germ removed from corn kernels, and pretreated biomass fibers transportation, pretreatment, milling, and mixing issues have been considered. Currently, corn stover is left on the fields, while wheat straw is either baled or left on the fields. The soy hulls, oat hulls, or corn germ meal and DDG/DDGS would be easily collected from the processing plants where they are produced; however, due to their low bulk density, the transportation costs for crop residues from the field to the thermochemical processing plant would be high unless these facilities are located within reasonable distances.

The transportation of the corn stover and wheat straw could be addressed by collection from the field and transportation to a central location within, for example but not limited to, a 30 mile radius. At that site, the thermochemical treatment could take place and the pretreated slurry or pretreated solids could be transported to the local feed mill where it could be mixed with the DDG/DDGS. The soy hulls, oat hulls, or corn germ meal could be treated similarly by pretreating the hulls or meal at the plant where they are produced. The pretreated biomass would have a higher bulk density, thereby decreasing the overall transportation costs.

The issues associated with the distribution of the DDG/DDGS could be reduced by building small dry mills distributed over a large area where corn is produced. This would decrease the distance that the corn feedstock would need to be transported as well as decreasing the distance that the DDG/DDGS would need to be transported. The local thermochemical pretreatment sites would also need to be distributed where the corn stover and wheat straw feedstocks are produced to decrease the distances of transportation.

The process of this invention represents an improvement over the background art dry-grind process for ethanol, in which the entire corn kernel is milled and processed, including the entire pericarp 120 and germ 125, which are carried through the fermentor. Removing some of the non-fermentables before fermentation, especially when combined with advanced fermentation technology, can increase the efficiency of fermentation and co-product dewatering. This will not only save money by using less energy for drying the co-products, but the co-products can be processed to obtain additional products. In the case of germ 125, the co-products removed by processing may be corn oil and tocopherols, and for pericarp 120, phytosterols may be extracted, depending with which fraction the aleurone layer remains. The value of these co-products also lowers the overall cost of ethanol production.

In the background art corn wet-milling process, corn is steeped with water and $SO_2$ for up to 48 hours. During the steeping, lactic acid-producing bacteria ferment a portion of the corn solubles. This process softens the kernel by allowing $SO_2$ and lactic acid to enter the corn kernel through the tip cap, which allows separation of the various parts of the corn by milling and density differences. The $SO_2$ and lactic acid hydrolyze the chemical bonds between the various components of the corn kernel and also help to break down the starch-protein matrix in the endosperm, allowing for efficient separation of the starch. As discussed above, the known in the art dry milling process simply grinds the entire kernel without separation of the components. The methods of the present invention include a process wherein the corn kernel is separated into its components without the use of large volumes of water and long steeping times employed in the background art, and, therefore represent an improvement over known art processes.

The process of this invention as described herein allows the diversion of the starch portion of the corn kernel for production of ethanol. The portions of the corn kernel not used in the production of ethanol are utilized as a component of the modified animal feed of this invention and which are supplemented with pretreated plant derived biomass fibers, such as for example but not limited to, soybean hulls, wheat straw and corn stover, to replace the starches diverted to ethanol production. The new animal feed of this invention contains a reduced amount of starch (a starch content of from about 5 to about 15 weight %) and will therefore not be as conducive to rumen acidosis thereby allowing the animal to utilize more of the animal feed of this invention. The hydration capacity of the treated biomass fibers of the animal feed of the present invention will allow for the addition of energy sources (e.g., DDG/DDGS and energy materials as described herein, preferably in the form of liquids) so that monogastrics have feed stuffs to replace a portion of the starch from corn.

EXAMPLES

Example 1

Dry Corn Fractionation

Corn milling tests have been conducted on dry fractionation of corn kernels at ADM. This run consisted of placing 5 kg of corn kernels in a rotating sealed vessel and adding 10% water. The vessel was rotated for 1 hour and then the kernels were removed. The tempered corn kernels were roughly ground through a ¼" Fitz Comminutor; followed by aspiration through a Kice aspirator with a 1" differential; the "overs" and "throughs" from the aspirator were sieved at 6, 12, and 20 mesh sizes. After sieving, the large particles from the "throughs" were roller milled twice at a gap setting of 1.1 on the Ferrell-Ross Flaking mill and then sieved at 6 and 12 mesh sizes. The fines (20 mesh or below) were combined prior to analysis. This produced 6 fractions as shown in Table 2 below.

The results show that the Fines are highly enriched in starch as compared to the native kernels, as well as enriched in NDF (neutral detergent fiber, equivalent to hemicellulose, cellulose and lignin) and depleted of fat and protein. This fines fraction is the largest fraction at 35.6%. Other samples enriched in starch include the Grits (33.6% of the yield) and Rolled Fines (10.1% of the yield). These fractions are also enriched in NDF and protein. The grits fraction is compositionally similar to the overall corn kernel composition.

TABLE 2

10% Moisture Tempered Corn—Fractions Compositions (%)

|  | Yield | Protein | Ash | Fat | NDF* | Starch |
| --- | --- | --- | --- | --- | --- | --- |
| Corn Kernels |  | 7.42 |  | 3.94 | 1.51 | 71.38 |
| Fines | 35.60 | 6.16 | 0.60 | 2.18 | 2.90 | 87.15 |
| Grits | 33.60 | 9.39 | 1.10 | 4.21 | 5.06 | 76.95 |
| Rolled Fines | 10.10 | 7.97 | 0.64 | 2.74 | 3.45 | 83.85 |
| Germ | 2.70 | 16.50 | 6.29 | 19.47 | 17.45 | 33.59 |

TABLE 2-continued

10% Moisture Tempered Corn—Fractions Compositions (%)

|  | Yield | Protein | Ash | Fat | NDF* | Starch |
|---|---|---|---|---|---|---|
| Pericarp | 10.00 | 8.78 | 1.68 | 3.97 | 43.30 | 36.57 |
| Rolled Pieces | 8.00 | 12.10 | 2.97 | 8.54 | 9.02 | 64.07 |

Example 2

Treatment of Biomass Fibers

Several biomass fibers have been obtained and have been prepared for experimentation. Wheat straw, rice hulls, rice straw, corn stover and oat hulls were ground in a Fitz Mill Comminutor (Chicago, Ill.) to a uniform size through a ½" screen. Distiller's dried grains with solubles, corn gluten feed (CGF), and soy hulls were also tested, but not ground.

The ground biomass fibers were treated with thermochemical treatments to increase biomass digestibility. Two treatments have been conducted, the first treatment with 10 w/w % calcium hydroxide and the second treatment with 2 w/w % ammonium hydroxide.

In the treatments with 10% calcium hydroxide, 1 kg (as-is basis) of each of the ½" ground biomass fibers were mixed with 100 grams of calcium hydroxide in a tumbler reactor and heated with direct steam injection to 145° C. for 30 minutes. The biomass fiber mixtures were removed from the reactor and the masses were recorded.

In the treatment with 2% ammonium hydroxide, 1 kg (as-is basis) of each of the ½" ground biomass fibers were mixed with 100 mL of 20% ammonium hydroxide in a tumbler reactor and heated with direct steam injection to 145° C. for 30 minutes. The biomass fiber mixtures were removed from the reactor and the masses were recorded. Table 3 details the amount of fiber solubilized by the treatment.

The treated biomass fiber samples were sent to the ADM Alliance Nutrition Research Center in Decatur, Ind. for analysis and determination of digestibility in cattle rumen. Samples were analyzed for 24-hour in situ dry matter (DM) and neutral detergent fiber (NDF) disappearance as well as typical chemical constituents (crude protein (CP), NDF, acid detergent fiber (ADF), acid detergent insoluble nitrogen (ADIN), neutral detergent insoluble nitrogen (NDIN), and ash). Samples were fermented in duplicate using a minimum of two animals and analysis of DM and NDF obtained for individual in situ bags as replication. Table 4 lists the composition of the fibers before and after pretreatment, and Table 5 details the change in digestibility of the fibers pre- and post-treatment.

The efficacy of CaOH and ammoniation was affected by sample type, but CaOH treatment was generally more effective than ammoniation under these processing conditions. When adjusted for initial ingredient values, increased fermentability of fiber was correlated with the decrease in hemicellulose due to treatment. This would be expected from base treatments and titration of ester bonds. Initial calculations of hemicellulose were negative for rice hulls, which is likely due to recovery of biogenic silica in the ADF procedure. Ash values were quite high for the rice hull samples and NDF was poorly digested regardless of treatment. Unexpectedly, ammoniation increased NDF content of the grain by-products. NDF insoluble nitrogen was also increased for these samples, suggesting increasing association of protein with fiber in this treatment. Dry matter and NDF digestion were improved with CaOH treatment for all treatments, although the effect on wheat straw was minimal. The effect of ammoniation on fiber digestion was variable with small improvements for several ingredients, decreased NDF digestion for rice hulls and corn stover, and substantial improvements for rice and wheat straws (numerically greater than CaOH). The rumen undigested protein (RUP) of treated samples was elevated for both chemical treatments, reflecting the effects of heat on rumen digestibility of protein.

These results suggest that CaOH treatment is more robust than ammoniation. Ammoniation can be considered for select ingredients but does not appear broadly applicable. Decreases in hemicellulose can be considered as a screening tool to rank treatment conditions.

TABLE 3

Solubilization Results for Biomass Fiber Experiments

| | | Ammonia Treatment | | | | Calcium Hydroxide Treatment | | | |
|---|---|---|---|---|---|---|---|---|---|
| | % Biomass Dry Solids | Added Mass (kg) | Dry Solids in Liquid, % | Dry solids Mass | % Solubilized | Added Mass (kg) | Dry Solids in Liquid, % | Dry Solids Mass | % Solubilized |
| Corn Stover | 88.1 | 5.5 | 2.08 | 114.4 | 13.0% | 5.665 | 3 | 169.95 | 19.3% |
| Wheat Straw | 89.4 | 5.17 | 1.75 | 90.5 | 10.1% | 4.9 | 3.39 | 166.11 | 18.6% |
| Oat Hulls | 86.65 | 5.13 | 1.25 | 64.1 | 7.4% | 5.595 | 3.15 | 176.24 | 20.3% |
| Soy Hulls | 93 | 5.26 | 4.41 | 232.0 | 24.9% | 5.26 | 5.25 | 276.15 | 29.7% |
| Rice Straw | 90.95 | 5.75 | 2.4 | 138.0 | 15.2% | 3.87 | 4.95 | 191.57 | 21.1% |
| Rice Hulls | 91.18 | 4.88 | 1.5 | 73.2 | 8.0% | 5.74 | 2.09 | 119.97 | 13.2% |
| DDGS | 91.65 | 7.07 | 5.45 | 385.3 | 42.0% | 5.42 | 8.35 | 452.57 | 49.4% |
| CGF | 89.35 | 6.17 | 6 | 370.2 | 41.4% | 5.205 | 7.4 | 385.17 | 43.1% |

TABLE 4

Effect of Ammoniation or Ca Hydroxide Processing on Sample Chemistry

| Ingredient | Native | CaOH | NH₃ | Average | Native | CaOH | NH₃ | Average |
|---|---|---|---|---|---|---|---|---|
| | NDF | | | | ADF | | | |
| CGF | 30.1 | 22.4 | 44.0 | 32.2 | 11.7 | 19.3 | 21.3 | 17.4 |
| Corn Stover | 75.7 | 60.7 | 69.0 | 68.5 | 50.3 | 55.1 | 49.6 | 51.7 |
| DDGS | 33.2 | 26.7 | 47.3 | 35.7 | 20.8 | 21.9 | 28.3 | 23.7 |
| Oat Hulls | 76.5 | 57.9 | 83.9 | 72.8 | 45.1 | 49.2 | 53.3 | 49.2 |
| Rice Hulls | 66.1 | 60.9 | 71.5 | 61.2 | 66.3 | 65.4 | 72.5 | 68.1 |
| Rice Straw | 62.0 | 64.1 | 55.4 | 60.5 | 52.2 | 56.6 | 46.7 | 51.8 |
| Soy Hulls | 64.5 | 64.3 | 72.8 | 67.2 | 48.8 | 59.9 | 64.6 | 57.8 |
| Wheat Straw | 68.7 | 72.3 | 61.0 | 67.3 | 53.0 | 54.3 | 52.8 | 53.4 |
| Average | 61.1 | 54.7 | 64.4 | | 44.1 | 48.2 | 49.5 | |
| | HemiCellulose¹ | | | | ADI-CP | | | |
| CGF | 18.4 | 3.1 | 22.7 | 14.7 | 1.6 | 5.4 | 4.9 | 4.0 |
| Corn Stover | 25.4 | 5.6 | 19.4 | 16.8 | 0.8 | 1.2 | 2.3 | 1.4 |
| DDGS | 12.4 | 4.8 | 19.0 | 12.1 | 6.2 | 7.9 | 12.3 | 8.8 |
| Oat Hulls | 31.4 | 8.7 | 30.6 | 23.6 | 0.3 | 0.8 | 0.8 | 0.6 |
| Rice Hulls | −0.2 | −4.5 | −1.0 | −1.9 | 0.8 | 1.1 | 1.2 | 1.0 |
| Rice Straw | 9.8 | 7.5 | 8.7 | 8.7 | 0.7 | 1.8 | 1.2 | 1.2 |
| Soy Hulls | 15.7 | 4.4 | 8.2 | 9.4 | 1.3 | 3.9 | 3.6 | 2.9 |
| Wheat Straw | 15.7 | 18.0 | 8.2 | 14.0 | 0.8 | 2.1 | 1.6 | 1.5 |
| Average | 17.0 | 6.4 | 15.0 | | 1.5 | 2.9 | 3.3 | |
| | NDI-CP | | | | Ash | | | |
| CGF | 4.3 | 7.3 | 6.5 | 6.0 | 7.4 | 21.2 | 8.4 | 12.3 |
| Corn Stover | 1.4 | 1.1 | 2.4 | 1.6 | 3.9 | 11.2 | 6.6 | 7.2 |
| DDGS | 4.9 | 10.3 | 16.6 | 10.6 | 4.2 | 16.9 | 4.0 | 8.4 |
| Oat Hulls | 0.8 | 0.9 | 1.1 | 0.9 | 5.8 | 11.3 | 5.9 | 7.7 |
| Rice Hulls | 0.9 | 1.3 | 1.5 | 1.2 | 17.3 | 21.6 | 18.1 | 19.0 |
| Rice Straw | 0.9 | 2.1 | 1.6 | 1.5 | 15.2 | 17.3 | 22.5 | 18.3 |
| Soy Hulls | 3.2 | 3.8 | 4.3 | 3.8 | 4.0 | 10.9 | 4.0 | 6.3 |
| Wheat Straw | 1.4 | 2.2 | 1.3 | 1.6 | 7.7 | 6.3 | 14.5 | 9.5 |
| Average | 2.1 | 3.4 | 4.1 | | 7.8 | 14.0 | 9.9 | |

¹Hemicellulose = NDF-ADF

TABLE 5

Effect of Ammoniation or Ca Hydroxide Processing on Rumen Digestion of DM, NDF and CP Dry Matter Digestion

| | (i) Treatments | | | | Improvement (x) | |
|---|---|---|---|---|---|---|
| | Native | CaOH | NH₃ | Ing. Ave. | CaOH | NH₃ |
| CGF | 78.6 | 93.1 | 80.9 | 84.2 | 1.18 | 1.03 |
| Corn Stover | 28.5 | 56.8 | 28.9 | 38.0 | 1.99 | 1.01 |
| DDGS | 63.5 | 85.5 | 73.9 | 74.3 | 1.35 | 1.16 |
| Oat Hulls | 24.6 | 52.9 | 20.9 | 32.8 | 2.15 | 0.85 |
| Rice Hulls | 13.2 | 26.2 | 9.2 | 16.2 | 1.99 | 0.70 |
| Rice Straw | 29.6 | 44.6 | 62.4 | 45.5 | 1.51 | 2.11 |
| Soy Hulls | 61.6 | 69.4 | 43.3 | 58.1 | 1.13 | 0.70 |
| Wheat Straw | 29.5 | 29.8 | 50.7 | 36.7 | 1.01 | 1.72 |
| Average | 39.3 | 56.5 | 44.0 | | 1.5 | 1.2 |

SEM = 2.4, SEM of ingredient averages = 2.0, SEM of treatment averages = 1.8

NDF Digestion

| | (ii) Treatments | | | | Improvement (x) | |
|---|---|---|---|---|---|---|
| | Native | CaOH | NH₃ | Ave | CaOH | NH₃ |
| CGF | 48.6 | 84.1 | 66.5 | 66.4 | 1.73 | 1.37 |
| Corn Stover | 22.9 | 44.0 | 13.8 | 26.9 | 1.93 | 0.61 |
| DDGS | 42.1 | 77.3 | 66.6 | 62.0 | 1.84 | 1.58 |
| Oat Hulls | 15.4 | 37.6 | 18.3 | 23.8 | 2.45 | 1.19 |
| Rice Hulls | 5.1 | 11.8 | 2.2 | 6.4 | 2.30 | 0.43 |
| Rice Straw | 15.5 | 35.1 | 47.7 | 32.8 | 2.27 | 3.08 |
| Soy Hulls | 51.5 | 58.4 | 34.3 | 48.1 | 1.13 | 0.67 |
| Wheat Straw | 17.2 | 18.3 | 35.2 | 23.6 | 1.06 | 2.04 |
| Average | 26.1 | 44.8 | 33.5 | | 1.8 | 1.4 |

SEM = 3.2, SEM of ingredient averages = 2.5, SEM of treatment averages = 2.3

RUP

| | (iii) Treatments | | | | Improvement (x) | |
|---|---|---|---|---|---|---|
| | Native | CaOH | NH₃ | Ave | CaOH | NH₃ |
| CGF | 87.0 | — | 93.3 | — | — | 1.07 |
| Corn Stover | 18.2 | 58.2 | 66.6 | 47.7 | 3.19 | 3.65 |
| DDGS | 48.6 | 76.9 | 73.6 | 66.4 | 1.58 | 1.51 |
| Oat Hulls | 42.9 | 69.2 | 51.0 | 54.3 | 1.61 | 1.19 |
| Rice Hulls | 38.9 | 29.1 | 36.9 | 35.0 | 0.75 | 0.95 |
| Rice Straw | 11.2 | 71.2 | 67.0 | 49.8 | 6.37 | 5.99 |
| Soy Hulls | 72.7 | 74.5 | 68.2 | 71.8 | 1.02 | 0.94 |
| Wheat Straw | 16.4 | 53.9 | 56.6 | 42.3 | 3.29 | 3.45 |
| Average | 42.0 | 61.9 | 64.2 | | 2.5 | 2.3 |

SEM = 4.1, SEM of ingredient averages = 3.3, SEM of treatment averages = 2.9

Example 3

Readco Processing of Wheat Straw and Corn Stover

The Readco processor is a double shaft mixer, which exerts mechanical shear on the material processed, leading also to increased temperatures. It could be an ideal processing device for impregnation of ammonia or other chemicals. Several treatments to increase the digestibility of the biomass samples were planned and they are shown in Table 6. The amount of chemical added could be less if the treatment distributes the chemical more effectively.

TABLE 6

Readco processing of wheat straw and corn stover

| Trt. # | Treatment | Amount added as a % of DM | Total Moisture |
|---|---|---|---|
| 1 | Anhydrous NH$_3$ | 3 | 35 |
| 2 | Anhydrous NH$_3$ | 6 | 35 |
| 3 | CaO | 2.5 | 35 |
| 4 | CaO | 5 | 35 |
| 5 | CaO | 10 | 35 |
| 6 | NaOH and H$_2$O$_2$ | 5 and 3 | 50 |
| 7 | NaOH and H$_2$O$_2$ | 2.5 and 1.5 | 50 |
| 8 | NaClO | 200 ppm | 30 |
| 9 | NaClO | 100 ppm | 30 |

Those skilled in the art shall appreciate that the present invention provides a method of processing corn kernels to obtain a high proof (from about 180 to about 190 proof) ethanol and a modified animal feed.

The methods and processes illustratively described herein may be suitably practiced in differing orders of steps. They are not necessarily restricted to the orders of steps indicated herein or in the claims.

As used herein and in the appended claims, the singular forms "a," "an," and "the" include plural reference unless the context clearly dictates otherwise.

Under no circumstances may the patent be interpreted to be limited to the specific examples or aspects or methods specifically disclosed herein. Under no circumstances may the patent be interpreted to be limited by any statement made by any Examiner or any other official or employee of the Patent and Trademark Office unless such statement was specifically and without qualification or reservation expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now known or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary and not intended as limitations on the scope of the invention.

Other objects, aspects, and embodiments will occur to those skilled in the art upon consideration of this specification, and are encompassed within the spirit of the invention as defined by the scope of the claims. Where examples are given, the description shall be construed to include but not to be limited to only to those examples. It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

We claim:

1. A method for processing corn kernels comprising the steps of:
    removing the pericarp from said corn kernels to obtain a pericarp enriched fraction;
    contacting at least one of the pericarp enriched fraction and a lignocellulosic by-product of agricultural processing with a fiber hydrolyzing agent to at least partially hydrolyze lignocellulosic fibers and obtain a treated fiber fraction;
    removing the germ from said corn kernels, resulting in a starch and a protein;
    separating said protein from said starch;
    liquefying and saccharifying and fermenting said starch to produce a fermented starch broth;
    recovering ethanol and distillers dried grains from the fermented starch broth; and
    combining the treated fiber fraction with the distillers dried grains to form a modified distiller's dried grain product.

2. The method of claim 1 including liquefying said separated starch before said saccharification and fermentation of said starch.

3. The method of claim 1 including wherein said step of removing said pericarp comprises the steps of:
    chemically separating said pericarp from the remainder of said corn kernel by alkali debranning, acid debranning, or gaseous or liquid ammonia addition of said corn kernel; and
    milling said separated pericarp.

4. The method of claim 1 including wherein said step of removing said pericarp comprises the steps of:
    conditioning said corn kernels with steam or hot water having a temperature from about 50° C. to about 99° C.; and
    milling said corn kernels to abrade and remove said pericarp.

5. The method of claim 1 including wherein step of removing said germ from said corn kernels comprises the steps of:
    utilizing a lactic acid steeping to hydrolyze the chemical bonds between the endosperm and said germ or utilizing enzyme hydrolysis to separate said germ from the endosperm; and
    milling said corn kernel to remove said germ.

6. The method of claim 1 comprising the steps of:
    processing said starch and protein to remove oils and sterols therefrom; and milling said starch to granularize said starch.

7. The method of claim 1 including wherein said step of separating said starch and protein is accomplished utilizing a method selected from a group consisting of clam shell processing, centrifuge processing, solubilization of said starch portion by enzyme saccharification, jet cooking and membrane filtration.

8. The method of claim 1 wherein obtaining the treated fiber fraction comprises contacting the pericarp enriched fraction with the fiber hydrolyzing agent.

9. The method of claim 8 wherein obtaining the treated fiber containing fraction further comprises contacting the lignocellulosic by-product of agricultural processing with the fiber hydrolyzing agent.

10. The method of claim 8 comprising the step of processing said pericarp enriched fraction to obtain pericarp by-products prior to contacting the pericarp enriched fraction wit the hydrolyzing agent.

11. The method of claim 10 including wherein said by-products of said pericarp processing include phytosterols, hemicelluloses, ferulic acid, and coumaric acid.

12. The method of claim 1 wherein obtaining the treated fiber fraction comprises contacting the lignocellulosic by-product of agricultural processing with the fiber hydrolyzing agent.

13. The method of claim 1 wherein the fiber hydrolyzing agent comprises at least one composition selected from the group consisting of calcium hydoxide, calcium oxide, sodium hydroxide, hydrogen peroxide, ammonia and a hypochlorite salt.

14. The method of claim 1 wherein the lignocellulosic by-product of agricultural processing comprises at least one member selected from the group consisting of corn gluten fiber, corn stover, distillers dried grains, oat hulls, rice hulls, rice hulls, rice straw, soy hulls, and wheat straw.

* * * * *